United States Patent
Nozaki (10) Patent No.: US 7,148,248 B2
(45) Date of Patent: Dec. 12, 2006

(54) METHOD OF TREATING OR INHIBITING THE DEVELOPMENT OF BRAIN INFLAMMATION AND SEPSIS

(76) Inventor: Masako Nozaki, 4-1-40, Kitanosawa, Minami-ku, Sapporo-shi, Hokkaido (JP)

( * ) Notice: Subject to any disclaimer, the term of this patent is extended or adjusted under 35 U.S.C. 154(b) by 414 days.

(21) Appl. No.: 10/721,742

(22) Filed: Nov. 26, 2003

(65) Prior Publication Data

US 2004/0167161 A1   Aug. 26, 2004

Related U.S. Application Data

(60) Provisional application No. 60/496,677, filed on Aug. 21, 2003, provisional application No. 60/429,558, filed on Nov. 29, 2002.

(30) Foreign Application Priority Data

May 20, 2003   (JP) ............................. 2003-142759

(51) Int. Cl.
*A61K 31/41*   (2006.01)
(52) U.S. Cl. ..................................... 514/382
(58) Field of Classification Search .................... None
See application file for complete search history.

(56) References Cited

U.S. PATENT DOCUMENTS

| | | | |
|---|---|---|---|
| 5,079,261 | A | 1/1992 | Serhan et al. |
| 5,441,951 | A | 8/1995 | Serhan |
| 2002/0123520 | A1 | 9/2002 | Marfat et al. |

FOREIGN PATENT DOCUMENTS

| | | |
|---|---|---|
| EP | 0351856 A2 | 1/1990 |
| EP | 0528337 A1 | 2/1993 |
| EP | 0905133 A1 | 3/1999 |
| EP | 1424101 A2 | 6/2004 |
| WO | WO 99/21007 | 4/1999 |
| WO | WO 02/06075 A1 | 8/2002 |

OTHER PUBLICATIONS

"Hemorrhagic Syndromes" and "Trauma of the Head". The Merck Manual of Diagnosis and Therapy (Seventeenth Edition). Merck & Co. Inc., 1999. p. 1424-1431.*

XP-001184701-Abstract, Hirabayashi et al., Cysteinyl leukotrienes activate microglia through the CYSLT1 receptor, *Society for Neuroscience*, 27(1)1160 (Nov.10, 2001).

Zeng et al., Yao Xue Xue Bao, Protective Effect of ONO-1078, A Leukotriene Antagonis on Foca Cerebral Ischemia in Mice, *Acta. Pharamaceutics Sinica*. 36(2):146-150 (2001) ABSTRACT Zhang, W., et al., Neuroprotective Effect of ONO-1078, A Leukotriene Receptor Antagonist, on Focal Cerebral Ischemia in Rats, *Acta Pharmacol Sin*, 23(10):871-877 (2002).

Alvarez Losada, Role of platelet-activating factor, eicosanoids and bradykinin in adjuvant therapy for sepsis, Acta Perdiatrica Espanola, 60(9):535-544 (2002).

Beers and Berkow, Merck manual of diagnosis and theapy, *Merck Research Laboratories*, 1435-1437 (1999).

Kobayashi et al., Effect of leukotriene antagonist on experimental delayed cerebral vasospasm, *Neurosurgery*, 31(3):550-556 (1992).

Matsuo et al., Leukotriene $B_4$ and $C_4$ in cerebrospinal fluid from children with meningitis and febrile seizures, *Pediatric Neurology*, 14(2):121-124 (1996).

Neuwelt et al., Use of enhanced computerized tomography to evaluate osmotic blood-brain barrier disruption, *Neurosurgery*, 6(1):49-56 (1980).

Ogata et al., Protective effects of a leukotriene inhibitor and a leukotriene antagonist on endotoxin-induced mortality in carrageenan-pretreated mice. *Infection and Immunity*, 60(6):2432-2437 (1992).

Yoshikawa et al., Effect of platelet-activating factor antagonist and leukotriene antagonist on endotoxin shock in the rat: role of the leukocyte, *Circulatory Shock*, 38:29-33 (1992).

Is there a therapeutic role for blood-brain barrier disruption? *Annals of Internal Medicine*, 93(1):137-139 (1980).

Abstract-XP002284974—*Derwent Publications Ltd.*, (1996).

* cited by examiner

*Primary Examiner*—Ardin H. Marschel
*Assistant Examiner*—Leslie A. Royds
(74) *Attorney, Agent, or Firm*—Browdy and Neimark, PLLC (57) ABSTRACT

A leukotriene C4 and D4 antagonist is used to treat or inhibit brain inflammation and sepsis by acting to inhibit increased capillary permeability and white blood cell extravasation. Potential candidate compounds can be screened in a non-human mammal before or after administration of an inflammation inducing agent into the subarachnoid space by determining their ability to inhibit increased capillary permeability and white blood cell extravasation.

7 Claims, 6 Drawing Sheets

Mechanisms of Action for Sepsis Therapies

METHOD OF TREATING OR INHIBITING THE DEVELOPMENT OF BRAIN INFLAMMATION AND SEPSIS

CROSS-REFERENCE TO RELATED APPLICATIONS

This application claims the benefit of priority under 35 U.S.C. §119(e) from U.S. provisional application No. 60/429,558, filed Nov. 29, 2002, and Ser. No. 60/496,677, filed Aug. 21, 2003, and claims the benefit of priority under 35 U.S.C. §119 (a–d) to Japanese patent application no. 142759, filed May 20, 2003, the entire contents of which are incorporated herein by reference.

BACKGROUND OF THE INVENTION

1. Field of the Invention

The present invention relates to a method for treating or inhibiting the development of a disease, disorder or condition, which is associated with increased capillary permeability and white blood cell extravasation, such as brain inflammation and sepsis.

2. Description of the Related Art

Arachidonic acid (AA) is released from phospholipid in the cell membrane to the cytoplasm in response to a number of insults such as mechanical, thermal, chemical, bacterial and other insults, and its products (the eicosanoid compounds prostaglandins and leukotrienes) have been found to be biologically important in a number of ways. Most of the eiconosaid compounds tend to aggravate inflammatory, pain, and fever responses, and they have been the targets of extensive research on anti-inflammatory and analgesic drugs. For example, anti-inflammatory steroids such as cortisone function by suppressing the phospholipase enzymes that generate arachidonic acid from membrane phospholipids. Pain-killers such as aspirin and ibuprofen act by blocking to some extent the cyclooxygenase enzymes that control the conversion of arachidonic acid to the eicosanoids, prostaglandins, prostacyclins, and thromboxanes.

Additionally, it is known that prostaglandins and leukotrienes contribute to the genesis of inflammation in both the peripheral and central nervous system (CNS). Despite studies done over three decades, exactly how prostaglandins contribute to inflammation remains unclear. In contrast, recent studies using leukotriene receptor antagonists indicate that leukotrienes might play a major role in this process.

Leukotrienes are potent lipid mediators and are divided into two classes, based on the presence or absence of a cysteinyl group. Leukotriene $B_4$ does not contain such a group, whereas leukotriene $C_4$, $D_4$, $E_4$ and $F_4$ are cysteinyl leukotrienes. These compounds have been recognized as inflammatory agents since the early 1980's (von Sprecher et al., 1993 and Piper, 1984).

In the 1990's, various drugs known as "leukotriene antagonists", which can suppress and inhibit the activity of leukotrienes in the body, were identified. The term "leukotriene antagonist" is used herein in the conventional medical sense, to refer to a drug that suppresses, blocks, or otherwise reduces or opposes the concentration, activity, or effect of one or more subtypes of naturally occurring leukotrienes. However, such leukotriene antagonists can be classified into two different groups based on a difference in mechanism of action, one which to suppresses 5-lipoxygenase and the other which competitively antagonizes the receptor for leukotriene. Pranlukast, which is one leukotriene antagonist, acts strictly at the leukotriene C4 and D4 receptor level.

Although some leukotriene receptor antagonists have been disclosed for use in treating brain inflammation (e.g., J63258-879-A, J02-169583-A, WO9959964-A1, EP-287-471-A), all of the disclosed leukotriene receptor antagonists are presumed to pass the blood-brain barrier (BBB) because it is conventional wisdom that a molecule must be able to pass the blood-brain barrier in order to reduce or inhibit brain inflammation, or to treat disorders of the brain resulting from brain inflammation (Wilkinson et al., 2001). As leukotriene $C_4$ and $D_4$ receptor antagonists do not pass the blood-brain barrier, insofar as is known, the leukotriene $C_4$ and $D_4$ receptor antagonists have never previously been used to treat or prevent brain inflammation except for a neuroprotective effect of pranlukast (ONO-1078), a leukotriene receptor antagonist, on focal cerebral ischemia in rats (Zhang et al., 2002) and in mice (Zeng et al., 2001). The leukotriene $C_4$ and $D_4$ receptor antagonists are, however, commonly used to treat asthma. The leukotriene $C_4$ and $D_4$ receptor antagonist pranlukast is used clinically as an anti-asthmatic drug and is known to have few side effects. Pranlukast does not pass, or passes the blood-brain barrier at most at a very minimal level, akin to the other antagonists such as zafirlukast and montelukast. Other off-label uses have been suggested for these compounds, including treatment of allergic diseases (Shih, U.S. Pat. No. 6,221,880) and for use in treating migraine and cluster headaches (Sheftell et al., U.S. Pat. No. 6,194,432).

Generally, capillaries are lined with endothelial cells that have various openings, such as intracellular clefts, fenestrae and pinocytotic vesicles. Unlike these general capillaries, brain capillaries are characterized by the relative absence of these openings between endothelial cells, but instead have tight junctions originated from the periphery. Furthermore, central capillaries are surrounded by astroglia cells, which are disposed over these tight junctions of endothelial cells (originating from the periphery). The blood-brain barrier (BBB) is a capillary barrier comprising a continuous layer of tightly bound endothelial cells. These cells permit a low degree of transendothelial transport, and exclude molecules in the blood from entering the brain on the basis of molecular weight and lipid solubility, as described in Neuwelt (1980). For example, the blood-brain barrier normally excludes molecules with a molecular weight greater than 180 daltons. In addition, the lipid solubility of molecules is a major controlling factor in passage through the blood-brain barrier.

The function of the blood-brain barrier is to maintain the homeostasis of the neuronal environment. Small molecules (M.W.<200 daltons) having a high degree of lipid solubility and low ionization at physiological pH freely pass through the blood-brain barrier. In addition, the blood-brain barrier allows water to move in either direction in order to maintain equal osmotic concentrations of solutes in the extracellular cerebral fluid.

The unique biological aspect of the blood-brain barrier is an important focus in treating central nervous system (CNS) disorders. While the interendothelial junctions between the cells of the blood-brain barrier are normally designed to keep potentially noxious substances away from the brain, this condition changes during inflammation. In other words, the permeability of the blood brain barrier increases. Brain inflammation, e.g., due to stroke or physical head injury, is a serious medical problem causing much human misery.

The therapeutic challenges posed by brain inflammation have been tackled using the following approaches: (1)

Osmotherapy, i.e., reducing the intracranial pressure by osmotic withdrawal of water from the brain tissue by intravenously administering such substances as mannitol, glycerol, urea to increase the osmolality of the blood brain barrier. Disadvantages include side effects such as electrolyte disturbances and renal failure. (2) Steroid therapy that reduces the local capillary leakage and global metabolic depression by means of compounds such as dexamethasone which easily crosses the blood brain barrier because of its lipid solubility. Disadvantages are manifold, such as gastrointestinal bleeding, electrolyte disturbances, hyperglycemia, reduction of immunocompetence, increased metabolic needs, and mental disturbances. (3) Nonsteroidal anti-inflammatory drugs that reduce local capillary leakage, such as indomethacin, probenecid and ibuprofen which cross the blood brain barrier. A disadvantage is that the pharmacological effect is not certain. (4) Anti-hypertension drugs that reduce the capillary leakage by lowering filtration pressure, by means of, e.g., nitroprusside. Disadvantages are the reduction of cerebral perfusion pressure and the changes for the worse for brain inflammation due to the increased capillary permeability of the blood brain barrier. However, none of these treatments improves brain inflammation.

To add to the difficulties faced by the clinician in treating brain inflammation, this condition does not present a unitary symptomatology. The inflammatory response in the brain occurs in three distinct phases, each apparently mediated by different mechanisms. First, there is an acute transient phase characterized by local vasodilation and increased capillary permeability. This is followed by a delayed, subacute phase, most prominently characterized by infiltration of leukocytes and phagocytic cells. Finally, a chronic proliferative phase sets in, in which necrosis of brain cells occurs, and glia cells appear where subsequently, however, its original function is lost.

Brain inflammation can be assessed by various techniques such as histochemistry and electron microscopy. However, the most significant parameter to quantify is probably the development of brain edema. Therefore, another approach has been to measure the amount of edema developed in injured tissue. Edema results from the influx of water caused by inflammation and is observed clinically as swelling. This can be quantified by comparing tissue before and after desiccation. The dry weight remaining after drying enables calculation of the amount of fluid evaporated. The fluid evaporated is the amount of edema that was formed.

Another common laboratory technique is to determine the influx of a water-soluble dye such as Evans blue albumin into the central nervous system. By coupling this to a fluorescent technique, the distribution of edema can be measured. More sophisticated and expensive methods such as PET (Positron Emission Topography), CT, MRI (Magnetic Resonance Imaging) as well as radioscintigraphy have been used as well.

However, the above methods can assess only the edema that is formed by the increased permeability of the blood-brain barrier, but they cannot assess the infiltration of leukocytes and phagocytic cells into the central nervous system. Overall, edema plays a very serious role in the pathology of brain inflammation by increasing the intracranial pressure, leading to damage of the brain tissue. Additionally, the increased permeability of blood vessels brings about brain edema, and then, infiltration of white blood cells (WBC) is induced, resulting in a more serious pathological condition, since lysosomal enzymes such as collagenase and esterase damage brain tissue directly. Therefore, determination of the changes in permeability of the blood brain barrier by means of measuring the cerebrospinal fluid (CSF) volume and the WBC count in CSF is essential.

As mentioned above, it has long been believed that in order to be effective in the brain, a drug must be able to cross the blood-brain barrier. Conventional targeting strategies have sought to circumvent this barrier either directly or indirectly, by administering prodrugs whose metabolites do cross the barrier or by attempting to disrupt the integrity of the blood-brain barrier in some way. See, e.g., Pardridge, (2002). To date, however, such a clinically effective agent has never been reported (Wilkinson et al., 2001).

There is therefore a need for a treatment that can be used on both an acute and a semi-acute basis to treat and inhibit the development of brain inflammation. The ideal compound or compounds would have minimal side effects including minimal invasiveness into the brain tissue. Additionally a method for monitoring the changes in WBC infiltration into the cerebrospinal fluid in animal models of brain inflammation would also be desirable.

Despite advances in supportive care and medical technology, the mortality rate from sepsis remains high. Sepsis is the most common cause of death in non-cardiac intensive care units, and its incidence appears to be rising. Over the last two decades, the prevailing belief has been that much of the morbidity and mortality of sepsis is attributable to the host's, extreme inflammatory response to bacteria or bacterial products. Indeed, sepsis is defined clinically as the presence of two or more conditions from the group making up what is known as the "Systemic Inflammatory Response Syndrome" (SIRS), manifested in response to a variety of severe clinical insults, these conditions being: a body temperature higher than 38° C. or lower than 36° C.; a heart rate greater than 90 beats per minute (bpm); a respiratory rate greater than 20 breaths/min. or $PaCO_2$ less than 32 torr (4.3 kPa); a white blood cell count of greater than 12,000 cells/$mm^3$ (leukocytosis), or less than 4,000 cells/$mm^3$ (leukopenia), or 10% of the total cell count being immature neutrophils or band neutrophils. This information is summarized in Table 1.

TABLE 1

Infection: Microbial phenomenon characterized by an inflammatory response to the presence of microorganisms or the invasion of normally sterile host tissue by those organisms.
Bacteremia: The presence of viable bacteria in the blood.
Sepsis: The systemic response to infection or trauma. This systemic response is manifested by two or more of (SIRS) conditions as a result of infection.
Severe sepsis: Sepsis associated with organ dysfunction, hypoperfusion or hypotension. Hypoperfusion and perfusion abnormalities may include, but are not limited to lactic acidosis, oliguria or acute alteration of mental status.

TABLE 1-continued

Septic Shock: Sepsis with hypotension, despite adequate fluid resuscitation, along with the presence of perfusion abnormalities that may include, but are not limited to lactic acidosis, oliguria or acute alteration of mental status. Patients who are on inotropic or vasopressive agents may not be hypotensive at the time that perfusion abnormalities are measured.
Sepsis induced hypotension: A systolic BP of <90 mm Hg or of >40 mm Hg from baseline in the absence of other causes for hypotension.
Multiple Organ Dysfunction Syndrome: Presence of altered organ function in an acutely ill patient such that homeostasis cannot be maintained without invention.

In pre-clinical animal studies, agents designed to limit this inflammatory response observed in sepsis have shown some initial promising effects. However, this initial promise has not been borne out in subsequent clinical investigations. Two main approaches have been taken: (1) Use of anti-inflammatory therapies; and (2) Use of anti-endotoxin therapies.

With respect to the use of anti-inflammatory therapies, at least three different types of agents have been found to directly limit the production or biologic effects of pro-inflammatory mediators. The agents of interest are: (1) steroids such as glucocorticoids; (2) antagonists or blockers of such pro-inflammatory cytokines as TNF-α and Interleukin-1β; and (3) antagonists or blockers of products generated during inflammation, such as bradykinin, or inflammatory mediators such as prostaglandin and platelet-activating factor (PAF).

With respect to steroids, such as glucocorticoids, a large dose of hydrocortisone has been shown to exacerbate an inflammatory response or to have no effect, but a smaller dose appears to have a beneficial effect even though it is not a sufficiently effective remedy for sepsis.

With regard to the blocking of specific cytokines, such as TNF-α and Interleukin-1β, it has been observed that despite promising results from animal studies, monoclonal antibodies to TNF-α or soluble TNF-α receptors have been shown to have no effect in clinical trials. Further, interleukin-1β receptor antagonists appear to have no beneficial effect in clinical trials.

Finally, it also appears that other mediator specific-inflammatory therapies including platelet-activating factor (PAF), bradykinin and prostaglandin, and the use of antagonists thereto were found to have no effect in clinical trials.

The second strategy targets bacterial products in the circulation with the expectation that neutralizing these bacterial toxins will limit the host pro-inflammatory response and thereby improve outcome. Substances employed include antisera, polyclonal antibodies and monoclonal antibodies.

Because pre-clinical animal studies limited the host pro-inflammatory response using both strategies, clinical trials for sepsis treatment were attempted. However, the clinical trials did not prove successful except for low dose steroid treatment. These findings are summarized in Table 2.

TABLE 2

| Medicine | Effect |
| --- | --- |
| 1. Anti-Inflammatory Therapy | |
| Glucocorticoids | |
| Hydrocortisone | |
| large dose (100 mg i.v. then 0.18/kg/hr) | none or worse |
| small dose (100 mg i.v./every 8 hours) | effective |

TABLE 2-continued

| Medicine | | Effect |
| --- | --- | --- |
| Mediator Specific Anti-Inflammatory Therapy | | |
| Anti-TNF-α | | |
| Monoclonal antibody to TNF-α | | none |
| Soluble TNF-α receptor antagonist | | none or worse |
| Anti-Interleukin-1 | | |
| Interleukin-1 receptor antagonists | | none |
| Other Mediator Specific Anti-Inflammatory Therapy | | |
| Anti-PAF | PAF Receptor Antagonist | none |
| Anti-Bradykinin | Bradykinin Antagonist | none |
| Anti-Prostaglandin | Cyclooxygenase Inhibitor | none |
| 2. Anti-Endotoxin Therapy | | |
| Antiserum | | none |
| Polyclonal Antibody | | none |
| Monoclonal Antibody | | none |

Furthermore, the mortality rate from sepsis is high (35–50%), in spite of this steroid treatment. It has been an important clinical priority to find an effective sepsis therapy.

The reasons for these findings might be a failure to monitor how anti-inflammatory agents act on each step of inflammation in the pre-clinical studies.

There is a major medical need for a treatment that can be used not only for treatment of chronic brain inflammation, but also on an acute and subacute basis, to treat, prevent or inhibit the development of brain inflammation. Furthermore, there is a major medical need for a treatment that can be used not only for treatment of chronic sepsis, but also on an acute and subacute basis, to treat, prevent or inhibit the development of sepsis. These are very serious, important, and unmet medical needs. The ideal compound or compounds would have minimal side effects.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF INVENTION

It is an object of the present invention to overcome deficiencies in the prior art, such as indicated above.

It is also an object of the present invention to provide a method for treating or inhibiting the development of a disease, disorder or condition which is associated with increased capillary permeability and white blood cell extravasations and selected from brain inflammation and sepsis, or the symptoms thereof, in a mammal in need thereof, where the method involves administering to a mammal in need thereof a therapeutically effective amount of a leukotriene C4 and D4 receptor antagonist.

The present invention involves the use of drugs that act as "leukotriene antagonists", viz., leukotriene C4 and D4 receptor antagonists. Accordingly, the present invention provides a method for short-term and semi-long-term and chronic yet safe administration of a drug that can treat, inhibit and/or prevent the development of brain inflammation and sepsis, or ameliorate the symptoms thereof, by administration of a therapeutically effective amount of a leukotriene C4 and D4 receptor antagonist, with the proviso that the brain inflammation is not focal cerebral ischemia.

The present invention also provides a method for screening an inhibitor of increased capillary permeability.

BRIEF DESCRIPTION OF THE DRAWINGS

FIG. 4A is rat #1 and FIG. 4B is rat #2.

DETAILED DESCRIPTION OF THE INVENTION

The present invention provides a method for treating or inhibiting the development of a disease, disorder or condition, which is associated with increased capillary permeability and white blood cell extravasation such as brain inflammation and sepsis, or for ameliorating the symptoms thereof, in a mammal in need thereof. The method involves administering to the mammal a therapeutically effective amount of a leukotriene C4 and D4 receptor antagonist, preferably pranlukast, or a pharmaceutically acceptable salt thereof, which does not cross or minimally crosses the blood brain barrier.

The term "leukotriene antagonist" is used herein in the conventional medical sense to refer to a drug that suppresses, blocks, or otherwise reduces or opposes the concentration, activity, or effects of one or more subtypes of naturally occurring leukotrienes. A leukotriene antagonist typically antagonizes the actions of leukotriene at the receptor level.

The present inventor has studied the inflammation mechanism with the use of leukotriene C4 and D4 receptor antagonists, in particular, pranlukast. Cyclooxygenase inhibitors (such as aspirin) are classified as Nonsteroidal Anti-inflammatory Drugs (NSAIDs) and are well known as a peripheral analgesics. However, it is difficult to show anti-edema effects of such cyclooxygenase inhibitors by measuring displacement water in rat paw edema method. It is known that pro-inflammatory cytokines (TNF-α, interleukin-1β and interleukin-6), inflammatory mediators and toxins produced by bacterias and/or viruses cause inflammation in sepsis. However, their corresponding antagonists of cytokines, anti-PAF, anti-bradykinin, NSAD and anti-endotoxin failed to inhibit the inflammation (Table 2).

Generally, when an inflammatory response develops, various cytokines and other inflammatory mediators act upon the local blood vessels, and increase the expression of endothelial CAM. It is believed that these pro-inflammatory cytokines and inflammatory mediators activate p-selectin and e-selectin on the endothelial cells of the capillary and then start the process of white blood cell extravasation that sequentially follows the steps of (1) Rolling, (2) Triggering, (3) Arrest/Adhesion, and (4) Transendothelial Migration.

TNF-α, interleukin-1 and interleukin-6 produced by activated macrophages at the site of the nociceptive stimuli play a particularly important role in mediating acute-phase inflammation as well as sepsis. In fact, proinflammatory cytokines administered to the outside of the blood brain barrier through the chronically in-dwelling intracerebroventricular catheter attached to an Ommaya reservoir increase white blood cell count (characterized by neutrophilic response and lymphocyte respectively) in the cerebrospinal fluid in dogs. The inflammation induced by interleukin-6, was longer lasting (starting from 2 hours, peak time are 10–24 hours lasting 24–72 hours) than that induced by interleukin-1β and TNF-α. In the present studies presented in the Examples hereinbelow, the inflammation caused by interleukin-6 was used as a sepsis model, measuring the amount of infiltrating white blood cells in the cerebrospinal fluid.

Of particular interest, the present inventor discovered that pranlukast (300 mg/kg, 500 mg/kg, 1000 mg/kg), which was orally administered 30 minutes before interleukin-6 was administered, completely inhibited interleukin-6 induced leukocyte in CSF for three days in the dog. In spite of the presence of interleukin 6 in the cerebrospinal fluid, the administration (p.o.) of pranlukast 30 min before interleukin 6 completely inhibited brain inflammation for 3 days. Furthermore, pranlukast inhibited brain inflammation induced by the administration of arachidonic acid in the subarachnoid space that increased capillary permeability and then, after 0.5–1 hour, also increased the extravasation of white blood cells to the CSF and the brain parenchyma in rats. These finding suggest that leukotriene $C_4$ and $D_4$ at the inside of the capillary plays an important role in the genesis of inflammation.

The process of inflammation is known as follows:

1) Macrophages activated by nociceptive stimulus secret TNF-α, interleukin-1β and interleukin-6 in tissues.

2) Vascular endothelial cells increase the expression of e-selectin by TNF-α, and interleukin-1β, and p-selectin by histamine and thrombin in the capillaries.

3) Circulating white blood cells express mucins such as PSGL-1 or the tetrasaccharides sialyl Lewis and sialyl Lewis$^a$ and sialyl Lewis$^x$, which bind to e- and p-selectin. This binding mediates the attachment or tethering of white blood cells to the vascular endothelium, allowing the cells to roll in the direction of the blood flow (Rolling). Although p-selection and sialyl Lewis-dependent alterations are induced by leukotriene C4/D4 in the mid-jejunum of rats, the leukotriene receptor antagonist was not effective (Samina Kanwar et al., (1995) . Since then, potent selectin inhibitors were developed; however, they have not yet succeeded (Alper J., 2001)

4) As white blood cells roll, chemokines (interleukin 8, MIP-1α/β, and MCP-1) and PAF, the complement split (C5a, C3a and C5b67) and various N-formyl peptide are produced. Binding of these chemoattractants to receptors on the white blood cell membrane triggers an activating signal mediated by G-proteins associated with the receptor. This signal induces a conformational change in the integrin molecules in the white blood cell membrane, increasing their affinity for immunoglobulin-superfamily adhesion molecules on the endothelium (Triggering).

(5) Subsequent interaction between integrin and immunoglobulin-superfamily CAMs stabilizes adhesion of the white blood cell to endothelial cell, enabling the cell to adhere firmly to the endothelial cell (Arrest/adhesion).

The white blood cell then migrates through the vessel wall into the tissue. The steps in transendothelial migration and how it is directed are still largely unknown. They may be mediated by molecules binding between the surface of white blood cell and CD31 on the capillary endothelial cell, or by the binding LFA-1 on the white blood cells and JAM on the capillary endothelial cell (Transendothelial Migration).

Thus, white blood extravasation is a sequential reaction and that is caused by interaction among capillary endothelial cells, molecules on the capillary endothelial cells, chemokines and adhesion molecules (selectin family, integrin family, and immunoglobulin-superfamily). However, it has not been previously known that leukotriene $C_4$ and $D_4$ play any role in the white blood cell extravasation in the central capillary.

The site of action of the leukotriene $C_4$ and $D_4$ receptor antagonist pranlukast is in the inside of the capillary lumen (involving the capillary endothelial cells) that is covered with the blood brain barrier in the central capillary.

Because pranlukast either does not cross or only minimally crosses the blood brain barrier, the anti-inflammatory effect of pranlukast is due to the inhibition of increased capillary permeability and the inhibition of white blood cells extravasation in the capillary lumen that involve adhesion of white blood cells to capillary endothelial cells, and the transendotherial migration of white blood cells. Thus, pranlukast inhibits brain inflammation without crossing the blood brain barrier. In the case of a brain inflammation that has increased the permeability of the blood brain barrier, pranlukast in the plasma can pass though the blood brain barrier which has increased the permeability and be delivered to the inflamed region.

In the general capillaries, the site of action of pranlukast is basically the same as that in central capillaries i.e., pranlukast has an anti-inflammatory effect through inhibition of white blood cell extravasation in the capillary lumen, involving adhesion of white blood cells to capillary endothelial cells, and the transendothelial migration of white blood cells. However, it may be distributed more widely in the peripheral tissues because the structure of general capillaries has more openings such as intracellular cleft, pinocytosis, and fenestra, compared to the structure of central capillaries.

Taken together, these findings and the previously disclosed data in Table 2 show that leukotriene $C_4$ and $D_4$ plays a more important role than proinflammatory cytokines, inflammatory mediators in the white blood cell extravasations in the capillary lumen involving adhesion of white blood cells to capillary endothelial cells, and the transendotheial migration of white blood cells in both brain inflammation and systemic inflammation. The leukotriene $C_4$ and $D_4$ receptor antagonist, pranlukast, competitively antagonizes the leukotriene $C_4$ and $D_4$ receptor and effectively inhibits brain inflammation (central inflammation) and sepsis (systemic inflammation).

The present inventor also discovered that dextran-induced rat paw edema was inhibited by pranlukast in a dose-dependent fashion. At a dosage of 450 mg/kg, administered intraperitoneally, pranlukast completely inhibited dextran-induced paw edema. This suggests that leukotriene C4 and D4 receptor antagonist acts at the endothelial cells in the capillaries and inhibits the increased permeability of the capillaries which is induced by dextran. In spite of the many openings such as clefts, fenestrae and pinocytotic vesicles in endothelial cells in the general capillary, pranlukast was found to inhibit peripherally the permeability. Since the endothelial cells in the brain capillaries have fewer openings because of the presence of the tight junctions, pranlukast may be more effective in inhibiting the permeability of brain capillaries than that of general capillaries. Therefore, it was expected that such a mechanism might also come into play at the central nervous system level.

To investigate the role of leukotriene $C_4$ and $D_4$ receptor antagonist in the treatment of brain inflammation, a sensitive and quantitative method to measure inflammation for the central nervous system was developed by the present inventor. According to this method, important changes in the inflammatory process induced by arachidonic acid can be monitored as follows: 1) the changes in permeability of blood-brain barrier (by measuring the amount (volume ($\mu$l)) of cerebrospinal fluid resulting from plasma component leaking through the blood brain barrier into the central nervous system) and 2) the infiltration of white blood cells into the cerebrospinal fluid (by counting the number of white blood cells using the hemacytometer) over time from the same experimental animal. In particular, the effect of the leukotriene $C_4$ and $D_4$ receptor antagonist, pranlukast, on brain inflammation was studied using this method. The administration of arachidonic acid as a nociceptive stimulus to cerebrospinal fluid showed the important changes in the inflammatory process of both the permeability of the blood brain barrier and the infiltration of white blood cells through the blood-brain barrier. Pranlukast inhibited these changes induced by arachidonic acid. It is known that leukotriene $C_4$ and $D_4$ receptor antagonists, such as pranlukast and zafirlukast as well as montelukast, either do not cross or minimally cross the blood-brain barrier. The present inventor has now confirmed that pranlukast acts directly or indirectly on endothelial cells in the blood brain barrier and inhibits capillary permeability to prevent leakage of plasma into the cerebrospinal fluid, and/or acts on the capillary lumen and inhibits white blood cell extravasations involving Rolling, Triggering, Arrest/adhesion and Transendothelial Migration. In the case of brain inflammation which results in increased permeability of the blood brain barrier, pranlukast in the plasma can distribute to the outside of brain capillary and can also act on the inflamed region in the central nervous system by crossing the blood brain barrier to inhibit brain inflammation. These findings are different from the widely held concept that the inhibitor for brain inflammation must cross or modulate the blood brain barrier for delivery to the inflamed region.

Figure 1:
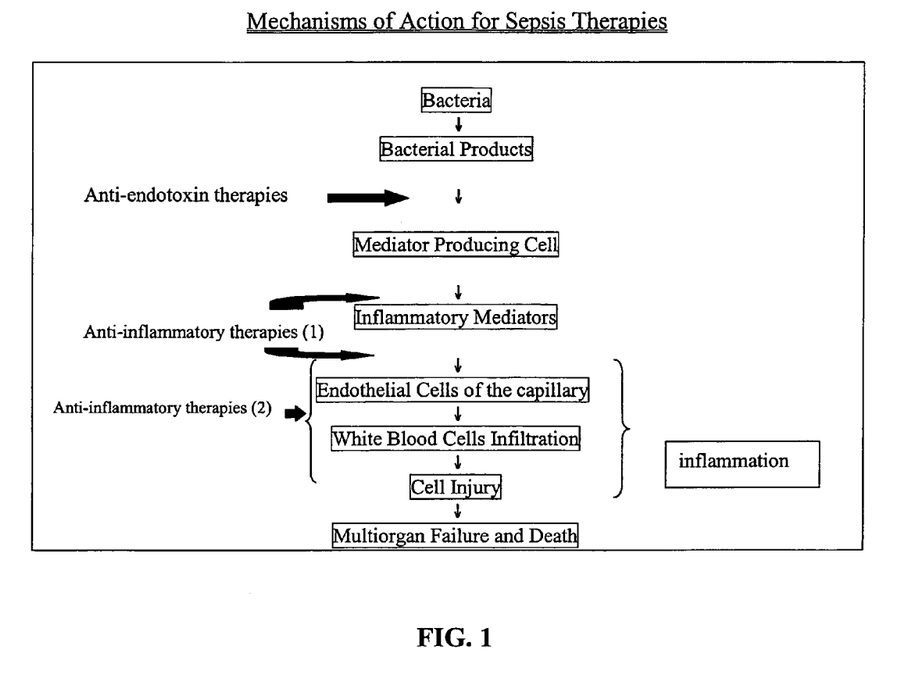
FIG. 1 is a schematic illustration of the mechanism of action for sepsis therapies.

The theory behind why leukotriene C4 and D4 receptor antagonists are inhibitors of increased capillary permeability and would therefore be useful for treating sepsis is presented in FIG. 1. As a leukotriene C4 and D4 receptor antagonist, pranlukast may be thought of as a new type of an anti-inflammatory drug (anti-inflammatory therapies (2) shown in FIG. 1) that acts on endothelial cells at the post-capillary venula and/or inside the post-capillary venula and provides a new therapy for sepsis that inhibits both central and peripheral inflammation.

The leukotriene C4 and D4 receptor antagonist pranlukast has been found to be safe ($LD_{50}$>2000 mg/kg (p.o.)) and (s.c.) in both rats and mice). After single administration of pranlukast (30 mg/kg, 100 mg/kg, 300 mg/kg, 1000 mg/kg; p.o.), and repeated administration of pranlukast (30 mg/kg/day, 100 mg/kg/day, 300 mg/kg/day, 1000 mg/kg/day; p.o.) for three months and six months, rats showed normal behavior, changes in body weight, and food intake compared with those of the control group. The results of urine examination and histopathological examinations are also normal by the single administration and the repeated administration of pranlukast. The maximum blood concentration of pranlukast (administered at 20 mg/kg) was attained within one hour after the administration (p.o.) and maintained for at least 5 hours. However, no pranlukast was observed 24 hours after administration of such low doses of pranlukast (data from Ono Pharmaceutical Co., Japan).

Zhang et al. (2002) reported that brain damage was induced by reperfusion 30 minutes after the occlusion of the middle cerebral artery (MCA) and was evaluated 24 hours after the reperfusion. Pranlukast (0.003 mg/kg–1.0 mg/kg) administered intraperitonealy 30 minutes before MCA and 2 hours after reperfusion inhibited the death of brain cells. However, Zhang et al. did not study blood concentrations. Indeed, no blood concentration of pranlukast would be found at 24 hours after the reperfusion at the dose levels (0.003 mg/kg–1.0 mg/kg) used by Zhang et al.

Generally, the severest brain damage develops 48–72 hours after the primary injury. This secondary injury is a result of the primary injury and is more serious than the primary injury. In most cases, the primary injury cannot be avoided and the secondary injury also cannot be prevented because there is no medication for brain inflammation. Large doses of pranlukast however stay longer in the blood over 24 hours and continuously inhibit the increased capillary permeability and white blood cell extravasations. Therefore, in order to avoid secondary injury a large dose of pranlukast needs to be administered. If the primary injury can be completely inhibited, then the secondary injury does not develop. Small doses (0.003–1.0 mg/kg) of pranlukast cannot inhibit the development of the secondary injury. Zhang et al (2002) reported that 0.1 mg/kg of pranlukast was the most effective dose in their study. This dose is equivalent to 6–8 mg in humans (body weight of humans is on average 60–80 kg) and is too low to be effective. It is expected that pranlukast at a dose of less than 100 mg/day does not provide a sufficiently effective anti-inflammatory effect.

Severe brain damage can be attenuated with large doses of pranlukast. Brain inflammation caused by a large dose of arachidonic acid (6.25 μg/2.0 μl) was not inhibited by pranlukast (450 mg/kg; p.o.) but was attenuated (white blood cell count returned to normal (=zero) 36 hours after arachidonic acid. Thus, brain inflammation caused by a large dose of arachidonic acid increased capillary permeability and increased white blood cell extravasation for 5 days without pranlukast. Administration of pranlukast (450 mg/kg) attenuated the brain inflammation and the duration of the brain inflammation).

As discovered by the present inventor, the inhibitors of brain inflammation, which do not cross or minimally cross the blood brain barrier, and the sites of action are:

(A) at the inside of the capillary, the pharmacological effect is as an anti-inflammatory agent (inhibition of the increased capillary permeability as well as the process of white blood cell extravasation from capillary to the tissue).

(B) at the outside of the capillary, in case of inflammation that has already increased capillary permeability, pranlukast is distributed with the plasma to the inflamed region because of the increased permeability of the blood brain barrier, and subsequently inhibits the brain inflammation.

The leukotriene $C_4$ and $D_4$ receptor antagonist pranlukast in the capillary inhibits inflammation even though there are pro-inflammatory cytokines and/or inflammatory mediators at the outside of the capillary.

The anti-inflammatory effect of leukotriene $C_4$ and $D_4$ receptor antagonist pranlukast that inhibits the increased capillary peameability and white blood cell extravasation from blood brain barrier into the central nervous system is superior to those of antagonists of pro-cytokines (TNF-$\alpha$, interleukin-1$\beta$ and interleukin-6 and other inflammatory mediators such as prostaglandin, PAF, and thromboxane).

As mentioned above, the anti-inflammatory effect of pranlukast inhibits the expression of p-selectin and/or e-selectin, leukocyte-specific cell adhesion molecules (CAMs) on endothelial cells or antagonizes leukotriene $C_4$ and $D_4$ that play an important role during white blood cell extravasasions in the capillary lumen.

According to the method of the present invention, a therapeutically effective amount of a leukotriene C4 and D4 receptor antagonist or a pharmaceutically acceptable salt thereof, which antagonist does not cross or minimally crosses the blood brain barrier, is administered to a mammal, preferably a human, in need thereof to treat or inhibit the development of a disease, disorder or condition associated with increased capillary permeability and white blood cell extravasation in brain inflammation and sepsis, or to ameliorate the symptoms thereof.

When the disease, disorder or condition to be treated or inhibited, or the symptoms thereof to be ameliorated, is brain inflammation, the present invention is not intended to include brain inflammation caused by focal cerebral ischemia when the leukotriene C4 and D4 receptor antagonist is pranlukast and is administered preferably in a dose that is about 400 mg/day to 800 mg/day in a low dose less than 100 mg/day. When pranlukast is preferably administered in a dose of about 400 mg/day to 800 mg/day then the brain inflammation need not exclude focal cerebral ischemia. It is intended that the disease, disorder or condition includes all other brain inflammations such as brain edema, stroke, hemorrhage (cerebral hemorrhage, subarachnoid hemorrhage, and subdural hematoma), Willis Circle occlusion syndrome, brain trauma (injury, trauma resulting from surgery and invasive brain operations), brain infection and encephalitis. In the case of encephalitis, the encephalitis may be primary encephalitis (by Japanese encephalitis virus, herpes simplex encephalitis, etc.), secondary encephalitis (by influenza virus, measles virus, chickenpox virus, rubella virus, etc.), and other subacute and chronic encephalitis. Non-limiting examples of encephalitis include acute disseminated encephalomyelitisitis, encephalomyelitisitis after vaccination, meningitis after vaccination, pululent meningitis, encephalomyelitis after infection, meningitis after infection, acute cerebellar ataxia, compression myelitis, acute ascending myelitis, acute myelitis, sclerosing myeitis, meningitic myelitis, meningoenchephalitis, myelitis, myelomeningitis, ventriculitis, meningitis, chronic meningitis. The brain inflammation is not particularly limited as long as it is due to leakage of white blood cells or the like from brain capillaries into surrounding tissues.

According to the present invention, sepsis is intended to include not only infectious diseases caused by bacteria, but also those caused by viruses. Food poisoning caused by various bacteria such as *Salmonella enteritidis, Clostridium botulinum*, etc., and severe acute respiratory syndrome (SARS) caused by Coronavirus are preferred examples. As Coronavirus mutates rapidly, developing an effective vaccine is difficult. Therefore, according to the present invention, a leukotriene C4 and D4 receptor antagonist can be administered to a patient when the patient comes down with SARS, thereby avoiding severe symptoms. Furthermore, brain inflammation due to an infection such as influenza encephalitis, encephalitis due to West Nile virus, cerebral meningitis including arachnoiditis are also included as sepsis.

It will be appreciated by those of skill in the art that the administration of the leukotriene C4 and D4 receptor antagonist in the method of the present invention can be performed pre-operatively before brain surgery or an invasive brain operation to prevent or inhibit brain inflammation or after the surgery or operation.

Furthermore, as the present invention inhibits not only increased capillary permeability but also increased white blood cell extravasation, the administration of the leukotriene C4 and D4 receptor antagonist can be repeated until the white blood cell count in the treated subject reaches a normal level in the cerebrospinal fluid.

The leukotriene C4 and D4 receptor antagonist used in the method of the present invention includes pranlukast (ONO-1078; Ono Pharmaceuticals, Osaka, Japan), zafirlukast and montelukast or a pharmaceutically acceptable salt and/or hydrate thereof. Pharmaceutically acceptable salts include alkaline metals such as lithium, sodium, potassium, etc., alkaline earth metals such as magnesium, calcium, etc., and aluminum. Non-limiting examples of other suitable leukotriene C4 and D4 receptor antagonists include the compounds, 8-[2-(E)-[4-(4-fluorophenyl)butyloxy]phenyl] vinyl [-4-oxo-2-]5–1H-tetrazolyl)-4H-1-benzopyran sodium salt (MEN-91507; Menarini), CR-3465 (Rottapharm), KP-496 (Kaken Pharmaceutical), 4-[6-acetyl-3-[3-[(4-acetyl-3-hydroxy-2-propylphenyl)thio]propoxy]-2-propylphenoxy]butanoic acid (MN-002; Kyorin Pharmaceutical; U.S. Pat. No. 4,985,585), and (R)-3-methoxy-4-[1-methyl-5-[N-(2-methyl-4,4,4-trifluorobutyl)carbamoyl]indol-3-ylmethyl]-N-(2-methyl phenylsulfonyl)benzamide(MCC-847; Astra Zeneca; EP 531078).

According to the method of the present invention, the magnitude of a prophylactic or therapeutic dose of a leukotriene C4 and D4 receptor antagonist in the acute or semi-chronic management of a disease, disorder or condition will vary with the severity of the condition to be treated and the route of administration. The dose, and perhaps the dose frequency, will also vary according to the age, body weight, and response of the individual patient. In general, suitable oral daily dosage ranges of leukotriene C4 and D4 receptor antagonists for mild trauma or for administration prior to brain surgery or an invasive can be readily determined by those of skill in the art. For example, see the Physician's Desk Reference, 54th Edition, Medical Economics Company Inc. (2000) for suitable dosages presently used for known leukotriene inhibitors for the treatment of asthma. For leukotriene C4 and D4 receptor antagonists, the oral daily dose range can be appropriately selected according to the symptoms of the patient. Specifically for pranlukast, the acceptable dose is preferably 100 mg/day–2000 mg/day, more preferably 200 mg/day–1000 mg/day, and most preferably 400 mg/day–800 mg/day.

In the case of pranlukast, there does not appear to be enough of an anti-inflammatory effect at a dose of less than 100 mg/day or 1 mg/kg/day of doses level. For montelukast, the dose range is preferably 5 mg/day–100 mg/day, more preferably 5 mg/day–50 mg/day, and most preferably 10 mg/day–20 mg/day. For zafirlukast, the dose range is preferably 10 mg/day–300 mg/day, more preferably 20 mg/day–150 mg/day, and most preferably 40 mg/day–80 mg/day. For more severe trauma or symptoms, higher doses may be administered.

It is further recommended that children, patients aged 65 years and older, and those with impaired renal or hepatic function initially receive low doses, and that they then be titrated up based on individual response(s) or the dose level in the blood. It may be necessary to use dosages outside these ranges in some cases, as will be apparent to those of skill in the art. Furthermore, it will be appreciated that the clinician or treating physician will know how and when to adjust, interrupt, or terminate therapy in conjunction with individual patient response.

The most common dosage form at present is an oral formulation for most presently available leukotriene antagonists because of the need to dissolve in stomach acid. Dosage forms may include tablets, troches, capsules, gel caps, lozenges, and the like. Due to their ease of administration, tablets and capsules represent the most advantageous oral dosage unit form, where solid pharmaceutical carriers are employed. In cases where the patient is unconscious, administration may preferably be by cannula to the stomach. If desired, tablets may be coated by standard aqueous or nonaqueous techniques. At least one presently available leukotriene C4 and D4 receptor antagonist, i.e., Singulair (montelukast), can be administered intravenously. Administration can be carried out once a day. Administration may be terminated when the white blood cell count in cerebrospinal fluid reaches a normal value.

A further aspect of the present invention is directed to a method for screening an inhibitor of increased capillary permeability for a mammal that does not cross or minimally crosses the blood brain barrier and that acts on vascular endothelial cells of capillaries and can inhibit increased capillary permeability and/or acts on the capillary lumen to antagonize white blood cell extravasations and prevent leakage of plasma components and blood cells from capillaries into tissues. The method includes the steps of: (1) administering a potential candidate inhibitor compound to a non-human mammal such as a rat, a mouse, a gerbil, a dog, a cat, a rabbit or monkey, before or after an inflammation-inducing agent is introduced into the subarachnoid space via a cannula inserted into the subarachnoid space through the dura mater of the brain of the non-human mammal; measuring the amount of cerebrospinal fluid collected through the cannula; and then determining from the measured amount of collected cerebrospinal fluid if the potential candidate inhibitor compound is an inhibitor of increased capillary permeability.

Examples of the inflammation-inducing agent include arachidonic acid, prostaglandin, thromboxane, histamine, yeast, LPS, dextran, bradykinin, carrageenan, leukotriene, TNF-$\alpha$, interleukin-1$\beta$ or interleukin-6. Among them, a low molecular weight compound such as arachidonic acid is preferred. In an animal model for sepsis, TNF-$\alpha$, interleukin-1$\beta$ or interleukin-6 is preferred for the inflammation-inducing agent. Further, a variety of substances are exemplified as the test substance mentioned above, however, leukotriene C4 and D4 receptor antagonist such as pranlukast is preferable. The method for administering a potential candidate inhibitor compound to a non-human animal is not particularly limited and can be selected appropriately from known administration methods such as oral administration, subcutaneous administration, intra-peritoneal administration, intravenous administration, intramuscular administration, nasal (nasal drop) administration, inhalation, sublingual administration, suppository administration, etc., in view of, for example, chemical properties (such as lipid-solubility, etc.) of the potential candidate inhibitor compound. The assessment of whether a potential candidate inhibitor compound can act on endothelial cells covering the inside of the capillary lumen to inhibit the increased capillary permeability and the infiltration of white blood cells from the capillary to the tissue can be conducted by measuring an amount of collected cerebrospinal fluid (extravasations of white blood cells that involves the adhesion of white blood cells to the capillary endothelial cells and the infiltration of white blood cells to the outside of the capillary). However, it is preferred that the white blood cell count in cerebrospinal fluid be measured together with the amount of cerebrospinal fluid. In addition, it is preferred that the cerebrospinal fluid is collected over time, e.g., every 30 minutes or one hour, and to assess the values relative to the controls (no administration of potential candidate inhibitor compound). Where the administration of the potential candidate inhibitor compound inhibits the exudation of cerebrospinal fluid and inhibits the presence of white blood cells in cerebrospinal fluid such as observed in the controls, then the potential candidate inhibitor compound can be regarded as an inhibitor of increased capillary permeability and is useful as a preventive agent for inhibiting increased capillary permeability when the inhibitor compound is administered prior to the introduction of an inflammation-inducing agent, and as an ameliorating agent when the inhibitor compound is administered after the introduction of an inflammation-inducing agent.

Only the potential candidate inhibitor compound is administered peripherally without any inflammation inducing agent to the interacerebroventricule in the screening method mentioned above. Using this system where the in-dwelling interacerebro/ventricular catheter attached to Ommaya reservoir, whether the potential candidate inhibitor compound crosses the blood brain barrier or not can be easily determined by measuring the amount of the potential candidate inhibitor compound in the cerebrospinal fluid over time with a known method such as ELISA or the like. The determination method is very useful for screening medical substances targeting treatment of the brain. In that case, a dog is preferable to a rat from the standpoint that it is possible to acquire a certain amount of cerebrospinal fluid.

The mechanism of the action of pranlukast, as demonstrated by the data presented below, stabilizes endothelial cells at the post-capillary venula in both the periphery and centrally and inhibits the permeability at the first phase in the process of inflammation. Inflammatory responses occur in three distinct phases, each apparently mediated by different mechanisms:
1. An acute transient first phase—vasodilation and increased capillary permeability.
2. A delayed subacute second phase—infiltration of leukocytes and phagocytic cells; and
3. A chronic proliferative third phase—necrosis of cells followed by substitution with glia cells in the central nervous system, and degeneration and fibrosis in peripheral areas.

A leukotriene C4 and D4 receptor antagonist, preferably pranlukast, can be used according to the present invention to treat or inhibit the development of brain inflammation and sepsis, and/or to ameliorate the symptoms thereof. This compound inhibits both peripheral and central inflammation due to its activity of decreasing the permeability of endothelial cells at the post capillary venula, thereby preventing or inhibiting leaking blood components at the first phase of inflammation. This anti-inflammatory mechanism of action of leukotriene C4 and D4 receptor antagonist is unique and can be clearly differentiated from conventional anti-inflammatory therapies and anti-endotoxin therapies (FIG. 1).

Anti-inflammatory Effect of Pranlukast in Peripheral Inflammation

Pranlukast inhibits dextran-induced paw edema in rats in a dose dependent manner. The administration of arachidonic acid to the subarachnoid space causes inflammation. However, pranlukast (p.o.) administered before arachidonic acid administration to the subarachnoid space inhibits inflammation. This may explain why pranlukast is effective and is different from anti-inflammatory therapies and anti-endotoxin therapies.

Having now generally described the invention, the same will be more readily understood through reference to the following examples which are provided by way of illustration and are not intended to be limiting of the present invention.

EXAMPLE 1

Peripheral Studies

Figure 2:
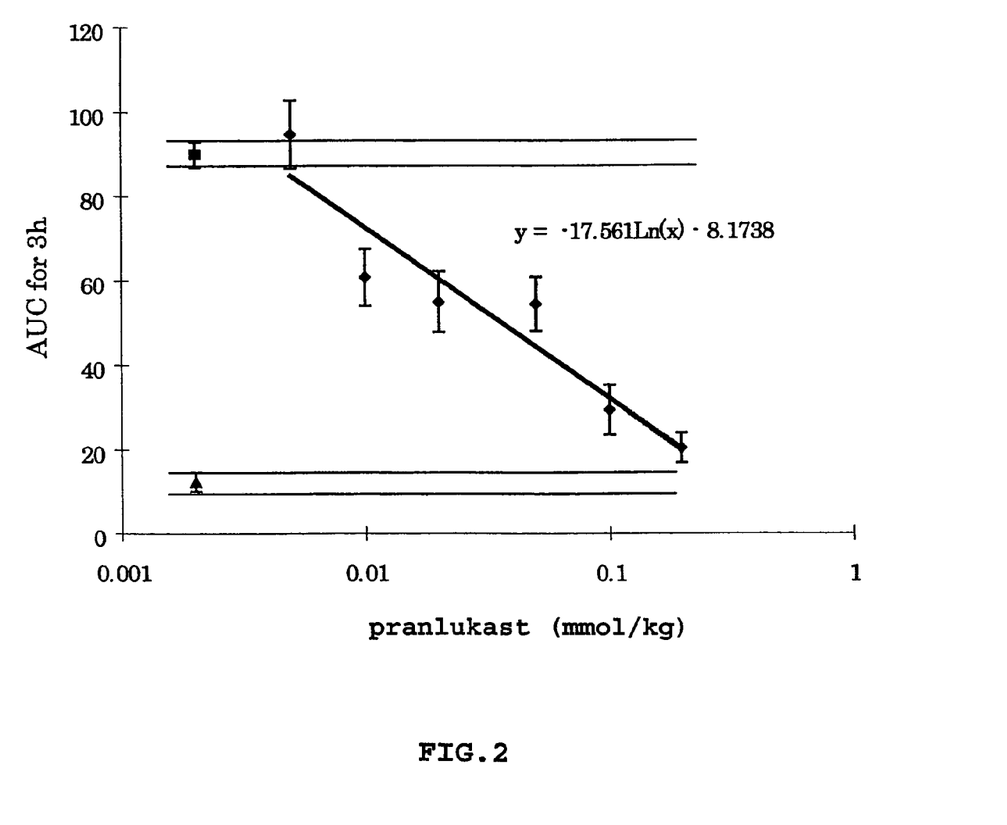
FIG. 2 is a graph depicting the action of ONO-1078 (pranlukast) on dextran-induced edema.

The present inventor discovered that dextran-induced rat paw edema was inhibited by pranlukast in a dose-dependent fashion. At a dosage of 450 mg/kg, administered orally, pranlukast completely inhibited dextran-caused paw edema (FIG. 2).

This suggested that LT antagonists might act at the endothelial cells in the peripheral capillary and inhibit the increased permeability of the capillary induced by dextran. In spite of the many openings such as clefts, fenestrae and pinocytic vesicles among endothelial cells in the capillary, pranlukast inhibited the permeability of the capillary. Since the endothelial cells in the brain capillary have less openings than other capillaries because of the presence of tight junctions, pranlukast may be more effective in inhibiting the permeability of the brain capillary than the permeability of a general capillary. Therefore, it is expected that such a mechanism might also come into play at the CNS level.

EXAMPLE 2

Measurement of Changes in the Inflammatory Process

To investigate the role of leukotriene antagonists in the treatment of inflammation, a sensitive and quantitative method to measure inflammation for the central nervous system was developed. Important changes in the inflammatory process can be monitored, as both the permeability of BBB and the infiltration of white blood cells (WBC) to cerebrospinal fluid (CSF) caused by arachidonic acid can be measured over time from the same experimental animal. In particular, the effect of the leukotriene C4 and D4 antagonist, pranlukast, was studied using this method. Changes in the inflammatory process of both the permeability of BBB and the infiltration of white blood cells (WBC) caused by administering arachidonic acid as a nociceptive stimulus were observed.

Materials and Methods

Figure 3:
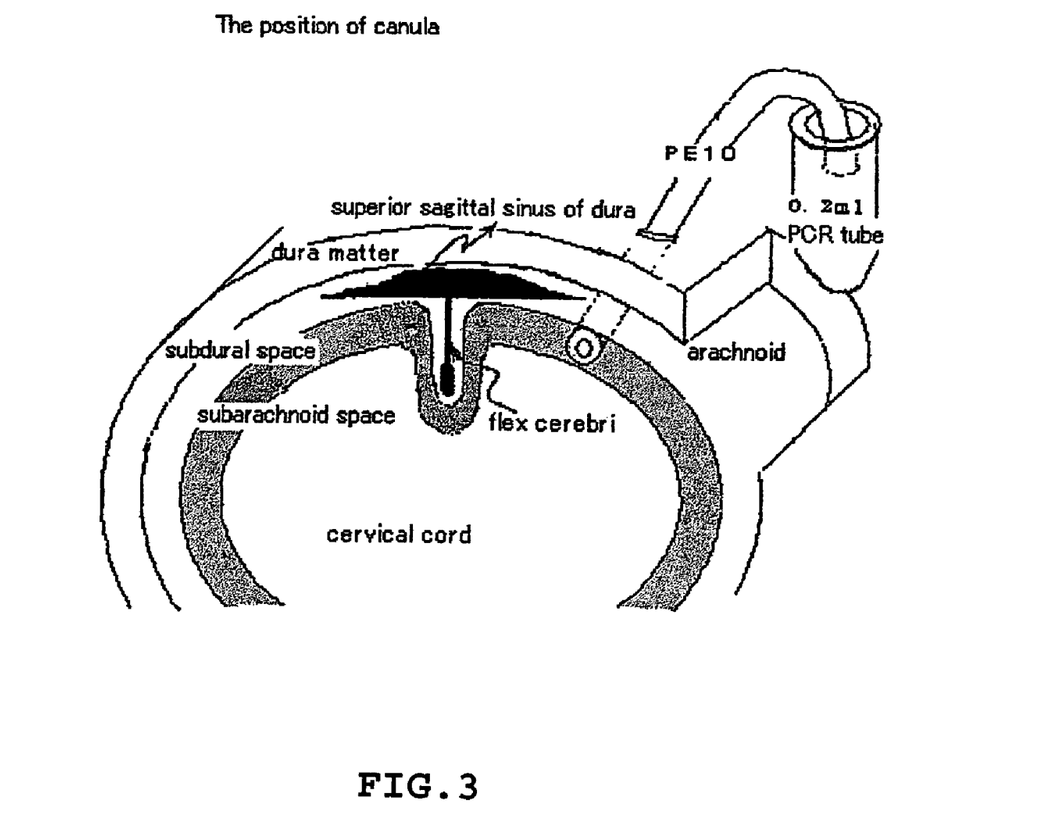
FIG. 3 is a schematic of the position of the cannula when measuring changes in the CSF of rats during the sepsis experiments.

Male rats, approximately 350–400 g, were anesthetized with sodium pentobarbital at a dose of 50 mg/kg intraperitoneally (i.p.). Animals were then placed in a stereotaxic unit. Fur from the top of the head to neck was shaved. The study area was disinfected with 70% ethanol followed by a 10% providone-iodine solution. Skin and muscle over the cervical cord were dissected until cervical vertebrae were exposed. A hole was made using a 23G3/4 needle passing through the dura via the cisterna magna. One end of a 2–3 mm PE10 cannula (0.011 "I.D., 0.007" thick, 0.024" O.D., 6.5 cm long) was inserted into the subarachnoid space at the cervical cord so as to avoid damage to neuronal tissue (FIG. 3). The cannula was fixed with cyanoacrylic glue to the peripheral tissue. The other end of PE10 was used for administration of a nociceptive stimulus, such as arachidonic acid (AA; 3.25 µg/2 µl) and subsequently for collecting cerebrospinal fluid (CSF) every thirty minutes thereafter during the 11-hour experimental period. The cannula filled with CSF immediately after the cannulation.

Air was infused to inject AA to the subarachnoid space. The muscles and skin were closed with surgical staples. The rat was then removed from the stereotaxic unit and placed on a heat pad and continuously monitored.

In the interaction study, the leukotriene C4 and D4 antagonist, pranlukast, was administered (450 mg/kg, i.p.) thirty minutes before administration of arachidonic acid (AA). If the effects of the anesthesia appeared to be wearing off, an additional 0.05–0.1 ml pentobarbital (50 mg/ml, i.p.) dose was administered. If at any time during the experiment, the animal appeared to be in pain or distress, the study was immediately stopped and the animal was euthanized.

After the experiment, the animal was euthanized by exposure to high concentration of halothane gas in an enclosed jar in a chemical fume hood.

Results

Figure 4A:
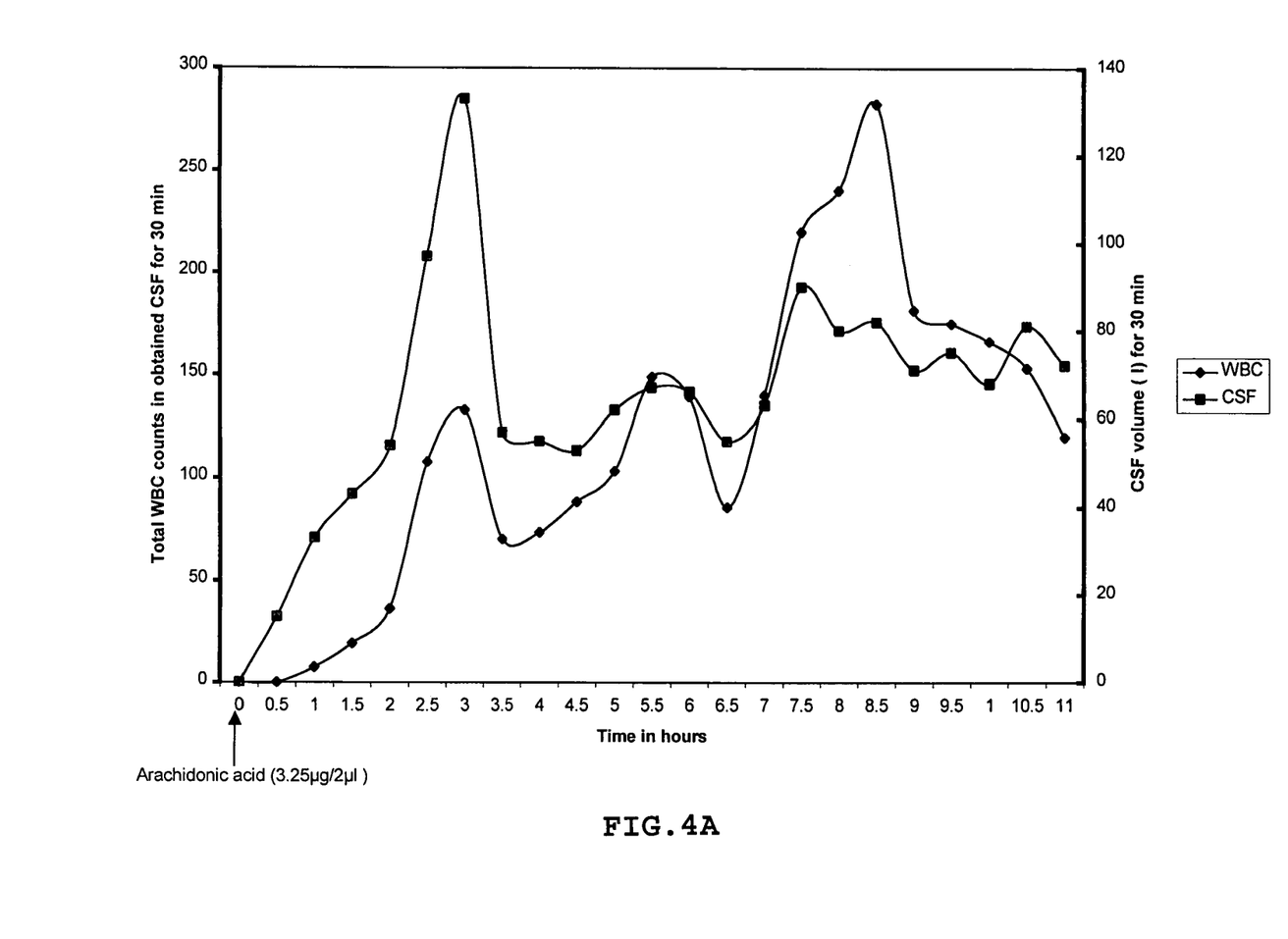
FIGS. 4A and 4B are graphs showing that the administration of arachidonic acid (3.25 µg/2 µl) causes inflammation in the central nervous system of two different individuals.
Figure 4B:
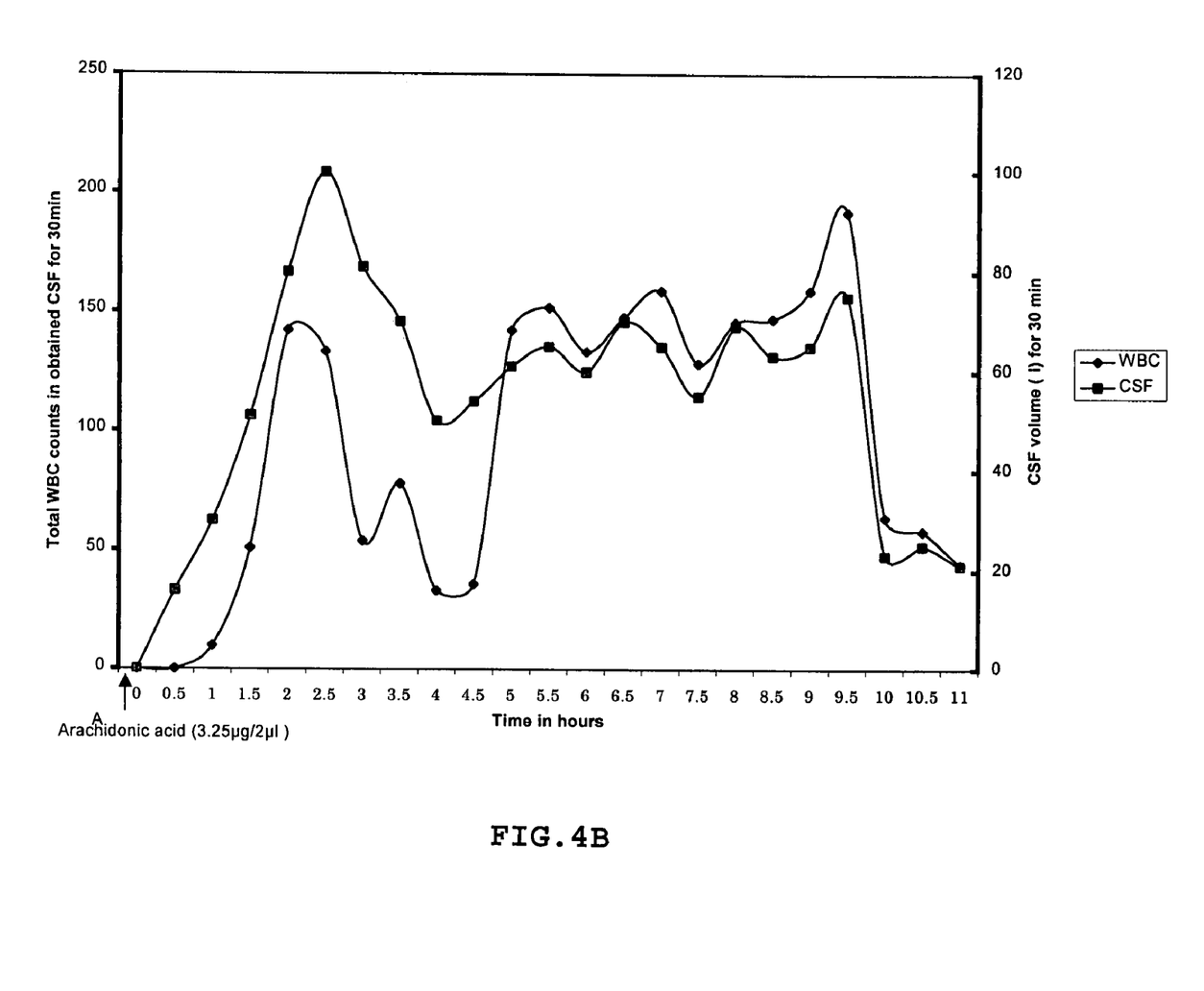

The volume of CSF increased immediately after the administration of arachidonic acid (3.25 µg/2 µl) to the subarachnoid space. CSF volume peaked within 3.5 hours (FIG. 4A and FIG. 4B). It gradually decreased 4–5 hours after the AA administration, but it was seen to remain at a continuous level during the 11-hour observation period at this dose level.

Infiltration of WBC was not seen within the first 30 minutes, which may implicate an acute transient phase of brain inflammation, but then started to increase slowly (FIGS. 4A and 4B). The changes of the total WBC counts and the volume of CSF rise and fall in parallel thereafter. This suggests a delayed subacute phase that is most characterized by the infiltration of leukocytes and phagocytic cells. Neither increased CSF nor WBC count was observed in the control animal. This was the normal state, as the pressure in the central nervous system is very low (6–10 mm Hg) and there are usually no WBCs in CSF.

Figure 5:
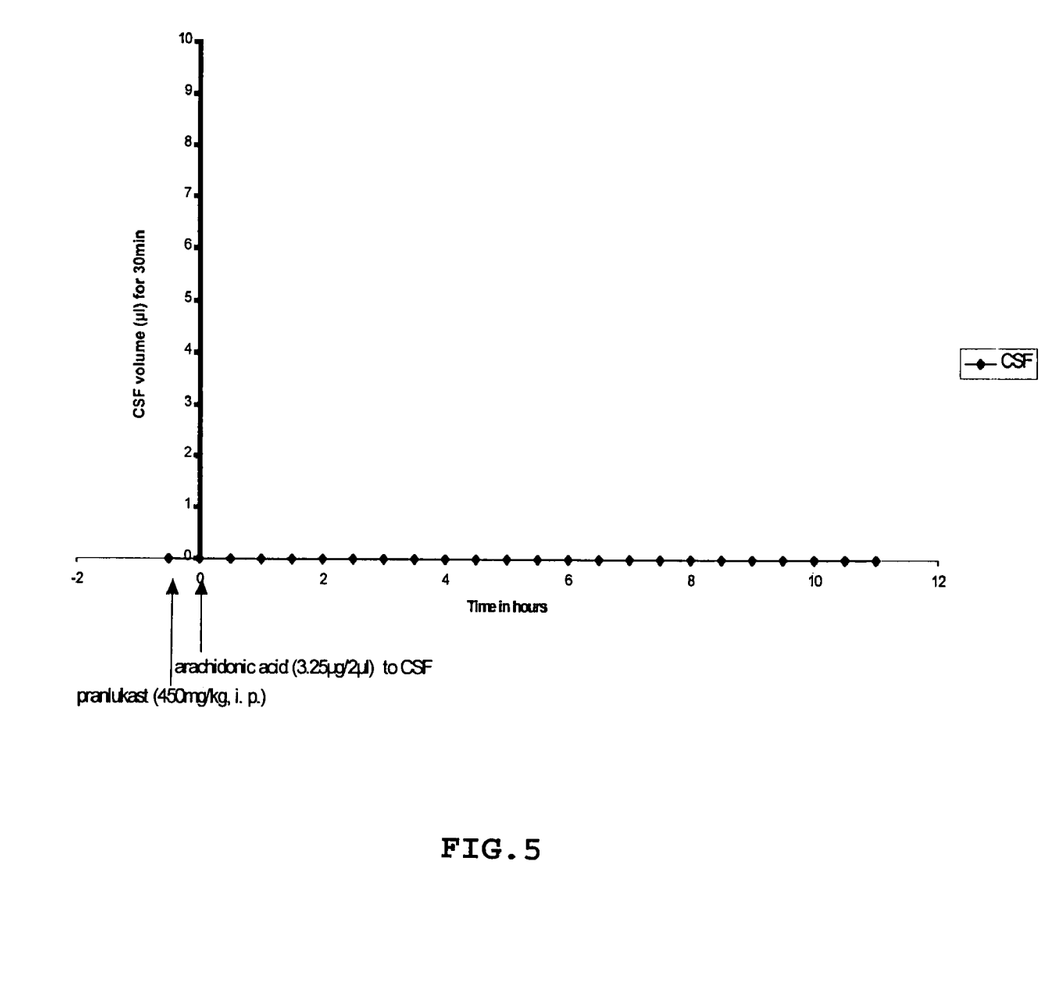
FIG. 5 is a graph showing the inhibitory effect of pranlukast (450 mg/kg, i.p.) on the inflammation caused by arachidonic acid (3.25 µg/2 µm) in the rat central nervous system (CNS). The data was obtained from four rats.

Pre-treatment using the leukotriene C4 and D4 receptor antagonist, pranlukast (450 mg/kg i.p.) thirty minutes before AA administration (3.25 µg/2 µl) completely inhibited the increase of CSF volume (n=4)(FIG. 5). This shows that pranlukast blocks an increase in the permeability of endothelial cells in the brain capillaries, as well as the infiltration of white blood cells.

EXAMPLE 3

Studies of the Effects of the Leukotriene Receptor Antagonist, Pranlukast

Evaluation of the Increases of the Permeability of Endothelial Cells in the Brain Capillaries and WBC Infiltration to the CSF during Inflammation Using the above-described method, it is possible to measure the changes in permeability over time in the same animal. No other method has been able to measure sepsis and inflammation over time using the same animals, and as a result, it has been necessary to sacrifice at least four animals (to attain statistical significance) at certain time periods. For example, if it is necessary to investigate the process of sepsis every thirty minutes for ten hours (n=4 for every thirty minutes), then 80 rats would need to be sacrificed. It is important to note that this method provides information not only regarding the changes in permeability of the brain capillaries, but also regarding changes in the infiltration of WBC into the CNS.

To obtain data on WBC infiltration into the CNS using this method, only four rats are required, avoiding the differences between individual animals for different time periods. Only this method can measure quantitatively both the permeability of the brain capillary and WBC infiltration into the CNS and can provide a more complete picture of the process of inflammation.

In the present study, the volume (µl) of cerebrospinal fluid (CSF) and white blood cell (WBC) counts in CSF was measured every thirty minutes for 11 hours from the same rat. One side of the cannula (PE10) was inserted into the subarachnoid space under pentobarbital anesthesia, avoiding neuronal damage (FIG. 3). If the brain tissue is damaged, the volume of CSF and WBC increases immediately without the administration of arachidonic acid. Since there are no WBC in the CSF in the normal rat, only rats that had no WBC in the CSF immediately after the cannulation were used. Another side of the cannula remained open and was used for the administration of nociceptive stimuli (arachidonic acid, LPS, dextran, etc.) and subsequently for collecting the CSF every thirty minutes during the experiment. The CSF volume was measured using a micropipette and WBC in the CSF were counted by means of a hemacytometer.

Arachidonic acid (3.2 µg/2 µl) increased the CSF volume immediately after administration, where a maximum volume of 100–120 µl was reached within 3.5 hours. Although the volume decreased thereafter, the CSF volume of 60–80 µl was maintained for every thirty minutes during 4.0–5.0 hours post-administration. WBC could not be detected for the first thirty minutes after the administration of arachidonic acid, but then was observed to increase gradually. The increase or decrease of WBC was followed by changes in CSF volume over time.

Pranlukast (450 mg/kg) was administered intraperitoneally thirty minutes before the arachidonic acid application into the subarachnoid space. Pranlukast completely inhibited the increase in CSF volume and in the permeability of the brain capillary marked by WBC infiltration.

The method characterized the first and second inflammatory phases as mentioned above, an acute transient phase characterized by local vasodilation and increased capillary permeability (first phase) and a delayed, subacute phase, most prominently characterized by infiltration of leukocytes and phagocytic cells (second phase).

The brain capillaries have a relative absence of pinocytotic vesicles, a greatly increased number of mitochondria, and the presence of tight junctions in capillaries, unlike general capillaries which have clefts, fenestrae and prominent pinocytic vesicles. It is known that leukotriene receptor antagonists pass the BBB at very minimal levels, if at all. This fact suggests that leukotriene receptor antagonists peripherally inhibit the permeability of the endothelial cells in the brain capillary. The endothelial cells are closely juxtaposed to one another and form tight junctions. These endothelial cells on the "inside" brain capillaries are much less likely to leak compared to those on general capillaries, since general capillaries have cleft passages, fenestrae and prominent pinocytic vesicles.

The treatment of brain inflammation by the leukotriene C4 and D4 receptor antagonist might be due to peripheral inhibition of the permeability of the endothelial cells between the capillary lumen and the BBB. Therefore, this ability to decrease brain capillary permeability and to inhibit infiltration of WBC into the central nervous system may be more important therapeutically than the drug being able to pass through the BBB or to open the BBB to allow drugs to access the brain inflammation. Once open, the BBB permeability will increase and contribute to the formation of brain edema as the pressure of the brain capillary is higher than the intercranial pressure. Furthermore, infiltration of blood components to the central nervous system potentiates brain inflammation.

These methods provide new findings as follows:
(1) The inflammatory process (phase 1 and phase 2) can be measured quantitatively over time by these methods; and
(2) Pranlukast inhibits the second brain injury as well.

EXAMPLE 4

Effect of Pranlukast and Other Anti-Inflammatory Drugs on Models of Traumatic Brain Injury in the Rat Pre-treatment of pranlukast has been found to result in longer survival in a rat ischemia model using a reversible 30 minute occlusion of both carotid arteries followed by reperfusion. One of 4–5 rats survived for one week when pranlukast (450 mg/kg i.p.) was administered 30 minutes before the occlusion.

Additionally, increased infiltration of WBC into the CSF caused by interleukin-6 were inhibited by pretreatment of pranlukast (administered at three different doses) in the intact dog.

It has now been discovered by the present inventor that the leukotriene C4 and D4 antagonist, pranlukast (450 mg/kg. i.p.), completely inhibits inflammation caused by arachidonic acid (3.25 µg/2 µl). This inflammation is the basis of increased permeability of the BBB and infiltration of WBC into the CSF. Therefore, the leukotriene C4 and D4 antagonist (pranlukast) is useful as a treatment of inflammation due to diseases, disorders and conditions such as stroke, brain trauma and the effects of brain surgery.

In view of the above and what is shown in Table 2, there is an inflammatory mechanism at the inside of capillary venulas that is controlled more strongly by leukotriene C4 and D4 than by cytokines such as interleukin 1β, TNFα and interleukin 6 at the outside of capillary venulas.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Alper J., Searching for Medicine's Sweet Spot, *Science,* 291:2338-2343 (2001)

Hardman, J. G., Limbird, L. E. and Goodman Gilman A., eds. *McGraw-Hill,* New York, pp. 3–29 (2001)

Neuwelt, E. A., "Is There A Therapeutic Role For Blood-Brain Barrier Disruption" *Ann. Int. Med.* 93: 137–139 (1980)

Pardridge, Drug and gene delivery to the brain. The vascular route, *Neuron,* 36:555–558 (2002)

Piper, Formation and actions of leukotrienes, *Physiol. Rev.,* 64(2):744–61 (1984)

Sialy Lewis, Dependent Alterations in Leukocyte Kinetics In Vivo, *Circulation Research,* 77(5):879–887 (1995)

von Sprecher et al., Strategies in the design of peptidoleukotriene antagonists, *J. Lipid Mediat.* 6:265–273(1993)

Wilkinson, G. R. Pharmacokinetics. In, Goodman and Gilman's The pharmacological Basis of Therapeutics. $10^{th}$ ed. (2001)

Zeng et al., Protective Effect of ONO-1078, A Leukotriene Antagonis on Foca Cerebral Ischemia in Mice, *Acta. Pharamaceutics Sinica,* 36(2):148–150 (2001)

Zhang, W., et al., Neuroprotective Effect of ONO-1078, A Leukotriene Receptor Antagonist, on Focal Cerebral Ischemia in Rats, Acta *Pharmacol Sin,* 23(10):871–877 (2002)

What is claimed is:

1. A method for treating or inhibiting the development of brain inflammation due to the trauma to the brain resulting from surgery, comprising administering to a mammal in need thereof a therapeutically effective amount of pranlukast or a pharmaceutically acceptable salt thereof, which does not cross or minimally crosses the blood brain barrier to treat or inhibit the development of brain inflammation due to trauma to the brain resulting from surgery.

2. The method of claim 1, further comprising repeating the administering step until the white blood cell count reaches a normal level in cerebrospinal fluid.

3. The method of claim 1, wherein the administering step is performed pre-operatively before brain surgery or before an invasive brain operation.

4. The method of claim 1, wherein the therapeutically effective amount of pranlukast is in a range of about 100 mg/day to 2000 mg/day.

5. The method of claim 1, wherein the therapeutically effective amount of pranlukast is in a range of about 200 mg/day to 1000 mg/day.

6. The method of claim 1, wherein the therapeutically effective amount of pranlukast is in a range of about 400 mg/day to 800 mg/day.

7. The method of claim 1, wherein the mammal is a human.

* * * * *